(12) United States Patent
Mathew et al.

(10) Patent No.: US 7,627,152 B2
(45) Date of Patent: Dec. 1, 2009

(54) IMAGE-BASED INDICIA OBFUSCATION SYSTEM AND METHOD

(75) Inventors: Prakash Parayil Mathew, Mukwonago, WI (US); Yaseen Samara, Palo Alto, CA (US); Vijaykalyan Yeluri, Sunnyvale, CA (US); Denny Wingchung Lau, Sunnyvale, CA (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 822 days.

(21) Appl. No.: 10/723,033

(22) Filed: Nov. 26, 2003

(65) Prior Publication Data

US 2005/0111762 A1 May 26, 2005

(51) Int. Cl.
*G06K 9/00* (2006.01)
(52) U.S. Cl. ...................................... 382/128
(58) Field of Classification Search ................. 382/128, 382/176, 177, 292, 282, 283
See application file for complete search history.

(56) References Cited

U.S. PATENT DOCUMENTS

| | | | | |
|---|---|---|---|---|
| 5,568,571 A * | 10/1996 | Willis et al. | ................. | 382/254 |
| 5,664,027 A * | 9/1997 | Ittner | ......................... | 382/170 |
| 6,735,347 B1 * | 5/2004 | Bates et al. | ................. | 382/282 |
| 6,823,203 B2 * | 11/2004 | Jordan | ......................... | 382/283 |
| 7,149,353 B2 * | 12/2006 | Siegel et al. | ............... | 382/190 |

* cited by examiner

*Primary Examiner*—Brian Q Le
(74) *Attorney, Agent, or Firm*—Fletcher Yoder

(57) ABSTRACT

A technique is provided for obfuscating or masking indicia viewable in a reconstructed image. Image data is acquired and stored and then accessed and the reconstructed image is analyzed to determine whether any indicia are viewable in the image that are in need of masking. Such indicia may include, for example, patient-identifying data. Other information may be left unmasked, such as orientation information, descriptive information, dates, and so forth. The technique permits automated recognition of indicia and altering of image data files so as to render certain sensitive information undecipherable in the processed reconstructed images.

22 Claims, 7 Drawing Sheets

US 7,627,152 B2

IMAGE-BASED INDICIA OBFUSCATION SYSTEM AND METHOD

BACKGROUND OF THE INVENTION

The present invention relates generally to medical imaging systems and techniques, and more particularly, to a technique for masking or obfuscating text or other indicia in medical images on an automated basis.

Many techniques are known for generating images in the medical diagnostics contexts. These include X-ray systems, computed tomography systems, magnetic resonance imaging systems, positron emission tomography systems, tomosynthesis systems, to mention just a few. In modern medical imaging, pixilated images are generated in digital formats. The pixilated images comprise rows and columns of pixels that are associated with one another in a matrix to define a useful image when reconstructed. The images typically depict anatomies and features of interest in diagnosing physical conditions, disease states, and so forth.

Medical diagnostics images are, however, sensitive in nature. Many such images not only illustrate the subject's anatomy, but provide user-readable indicia of various parameters and information. Certain information may be encoded into a header in a data stream. Such header information is well-known format, and sensitive information may be easily deleted from the header data. More problematic, however, are indicia that are provided in the image itself. Such indicia may be defined by contrasting pixels which, together, form letters or other indicia that are decipherable by human readers. The indicia typically provide some identification of the patient, as well as date, description, and other useful data for the medical professionals involved in producing the images and diagnosing the patient condition.

Due to the highly private and sensitive nature of medical images, however, laws and ethical consideration dictate that certain information should be removed from the images, and indeed from the patient records. It is desirable, for example, to remove information from diagnostic images that could uniquely identify a particular patient. However, where pixilated information is encoded into the image itself, removal or masking of the indicia can be extremely time consuming and imprecise.

There is a need, therefore, for an improved technique for obfuscating or masking indicia in medical diagnostics and similar images that can be implemented on an automated basis. There is a particular need for automated systems for removing, covering, or otherwise masking patient identification data in medical diagnostics images.

BRIEF DESCRIPTION OF THE INVENTION

The present invention provides a highly flexible and efficient automated technique that responds to such needs. The technique may be employed in a wide range of settings, but is particularly well-suited to medical diagnostic imaging applications where sensitive information, such as patient identification should not appear in certain stored, transmitted and reconstructed images. In general, the technique is applicable to digitized images, although any image source may serve as the originating system for the image data. That is, the technique may be used with X-ray images, CT images, MRI system images, PET images, tomosynthesis images, or any other suitable images which may bear contrasting pixels forming indicia which should be rendered undecipherable in a reconstructed and viewable image.

The invention contemplates methods, systems and computer programs designed to implement such techniques.

DETAILED DESCRIPTION OF SPECIFIC EMBODIMENTS

Figure 1:
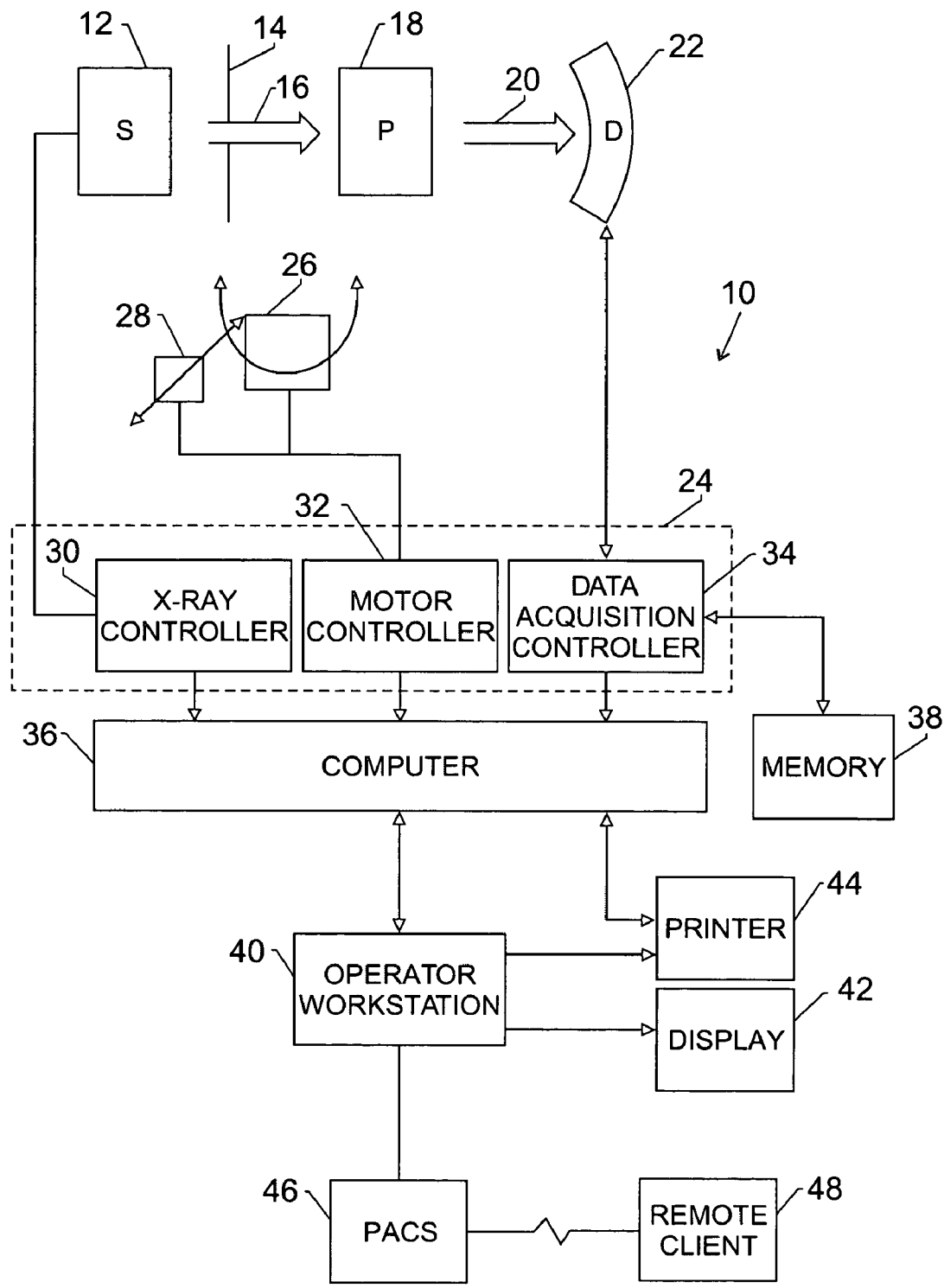
FIG. 1 is a diagrammatical view of an exemplary imaging system, in the form of a CT imaging system, for use in producing images from which indicia are to be removed or masked in accordance with aspects of the present technique.

FIG. 1 illustrates diagrammatically an imaging system 10 for acquiring and processing image data for which navigational images may be generated, as described in detail below. In the illustrated embodiment, system 10 is a computed tomography (CT) system designed both to acquire original image data, and to process the image data for display and analysis while the CT system 10 is described herein as one source of image data for which navigational images may be generated, it should be borne in mind that other imaging modalities may be employed as well, such as MRI systems, X-ray systems, ultrasound systems, PET systems, and so forth.

In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube. Collimator 14 permits a stream of radiation 16 to pass into a region in which a subject, such as a human patient 18 is positioned. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject. Moreover, the processed and stored reconstructed image will typically bear indicia, such as patient-identifying indicia, which is masked or obfuscated as described below.

Source 12 is controlled by a system controller 24, which furnishes both power and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and rotational subsystem 28. The rotational subsystem 28 enables the X-ray source 12, collimator 14 and the detector 22 to be rotated one or multiple turns around the patient 18. It should be noted that the rotational subsystem 28 might include a gantry. Thus, the system controller 24 may be utilized to operate the gantry. The linear positioning subsystem 26 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 and moreover, to a memory 38. It should be understood that any type of memory to store a large amount of data might be utilized by such an exemplary system 10. Moreover, the memory 38 may be located at this acquisition system or may include remote components for storing data, processing parameters, and routines described below. Also the computer 36 is configured to receive commands and scanning parameters from an operator via an operator workstation 40 typically equipped with a keyboard and other input devices. An operator may control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image and to control imaging. Additionally, the scanned image may also be printed by a printer 44 which may be coupled to the operator workstation 40. The display 42 and printer 44 may also be connected to the computer 36, either directly or via the operator workstation 40. Further, the operator workstation 40 may also be coupled to a picture archive and communications system (PACS) 46. It should be noted that PACS 46 might be coupled to a remote system 48, radiology department information system (RIS), hospital information system (HIS) or to an internal or external network, so that others at different locations may gain access to the image and to the image data. Additional components and functions of the PACS are set forth below.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
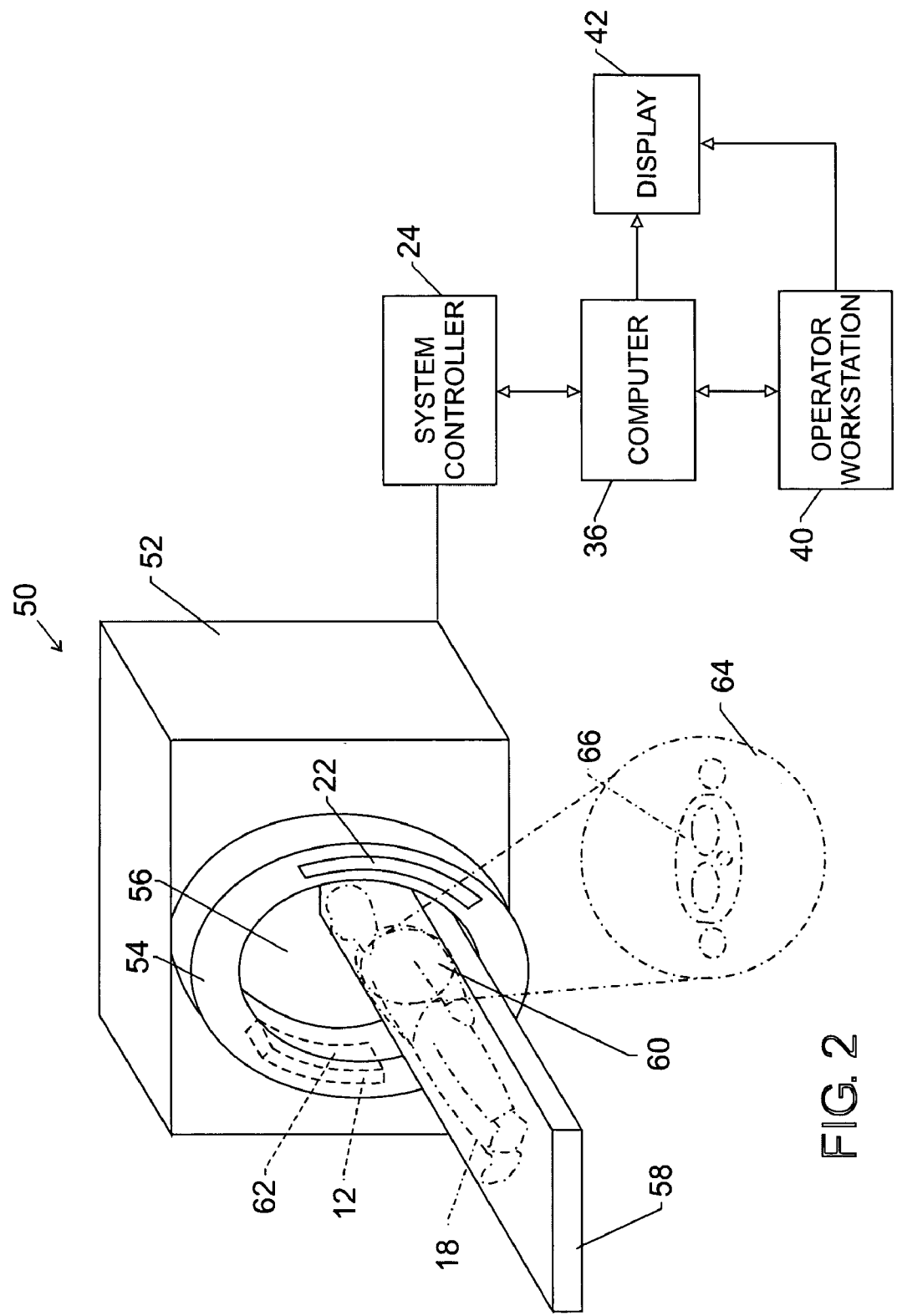
FIG. 2 is another diagrammatical view of a physical implementation of the CT system of FIG. 1.

Referring generally to FIG. 2, the exemplary imaging system of FIG. 1 is illustrated in a form typically used to generate medical images. The CT scanning system 50 is typically a multi-slice detector CT (MDCT) system that offers a wide array of axial coverage, high gantry rotational speed, and high spatial resolution, all of which allow the use of sophisticated image reconstruction algorithms. The CT scanning system 50 is illustrated as including a frame 52 and a gantry 54 with an aperture 56. The aperture 56 may typically be 50 cm in diameter. Further, a patient table 58 is illustrated positioned in the aperture 56 of the frame 52 and the gantry 54. The patient table 58 is adapted so that a patient 18 may recline comfortably during the examination process. Additionally, the patient table 58 is configured to be displaced linearly by the linear positioning subsystem 26 (see FIG. 1). The gantry 54 is illustrated with the source of radiation 12, typically an X-ray tube that emits X-ray radiation from a focal point 62.

In typical operation, X-ray source 12 projects an X-ray beam from the focal point 62 and toward detector array 22. The detector 22 is generally formed by a plurality of detector elements, which sense the X-rays that pass through and around the subject. Each detector element produces an electrical signal that represents the intensity of the X-ray beam at the position of the element at the time the beam strikes the detector. Furthermore, the gantry 54 is rotated around the subject of interest so that a plurality of radiographic views may be collected by the computer 36. Thus, an image or slice is computed which may incorporate, in certain modes, less or more than 360 degrees of projection data, to formulate an image. The image is collimated to desired dimensions, typically less than 40 mm thick using either lead shutters in front of the X-ray source 12 and different detector apertures. The collimator 14 (see FIG. 1) typically defines the size and shape of the X-ray beam that emerges from the X-ray source 12.

Thus, as the X-ray source 12 and the detector 22 rotate, the detector 22 collects data of the attenuated X-ray beams. Data collected from the detector 22 then undergoes pre-processing and calibration to condition the data to represent the line integrals of the attenuation coefficients of the scanned objects. The processed data, commonly called projections, are then filtered and backprojected to formulate an image of the scanned area. As mentioned above, the computer 36 is typically used to control the entire CT system 10 (see FIG. 1). The main computer that controls the operation of the system may be adapted to control features enabled by the system controller 24. Further, the operator workstation 40 is coupled to the computer 36 as well as to a display, so that the reconstructed image may be viewed. Alternatively, some or all of the processing described herein may be performed remotely by additional computing resources based upon raw or partially processed image data.

The system 10 (see FIG. 1) thus generates multiple images from acquired image data. Each reconstructed image corresponds to a slice 60 which, when cast in pixilated format, becomes a separate image related to other images sequentially in the imaged volume. For each image 60, then, within an image area or field of view 64, certain features of interest 66 will be visible.

As will be appreciated by those skilled in the art, the CT system acquires data continuously, although at discrete image view frames corresponding to specific angular positions, as the source and detector rotate about the subject. Moreover, in helical modes of operation, the data are collected as the subject is displaced by movement of the table. The resulting data set contains a large quantity of data points representative of the intensity of radiation impacting elements of the detector at each of the angular positions. Reconstruction of images proceeds by selecting desired "reconstruction windows" or spans of data points which, based upon the reconstruction algorithm employed, provide sufficient information to calculate locations of features causing X-ray attenuation. Such reconstruction techniques may employ windows spanning all 360° of angular positions, but for reasons of computational efficiency and to reduce the incidence of motion-induced artifacts, reconstruction algorithms generally rely upon windows spanning 180° plus the included angle of the X-ray beam (typically referred to as the fan angle or "α"). Due to redundancy in the data, such reconstruction windows generally suffice for image reconstruction and provide improved temporal resolution. Other techniques may employ a combination of data acquired during a plurality of shorter windows, such as in techniques referred to as multi-sector reconstruction.

Figure 3:
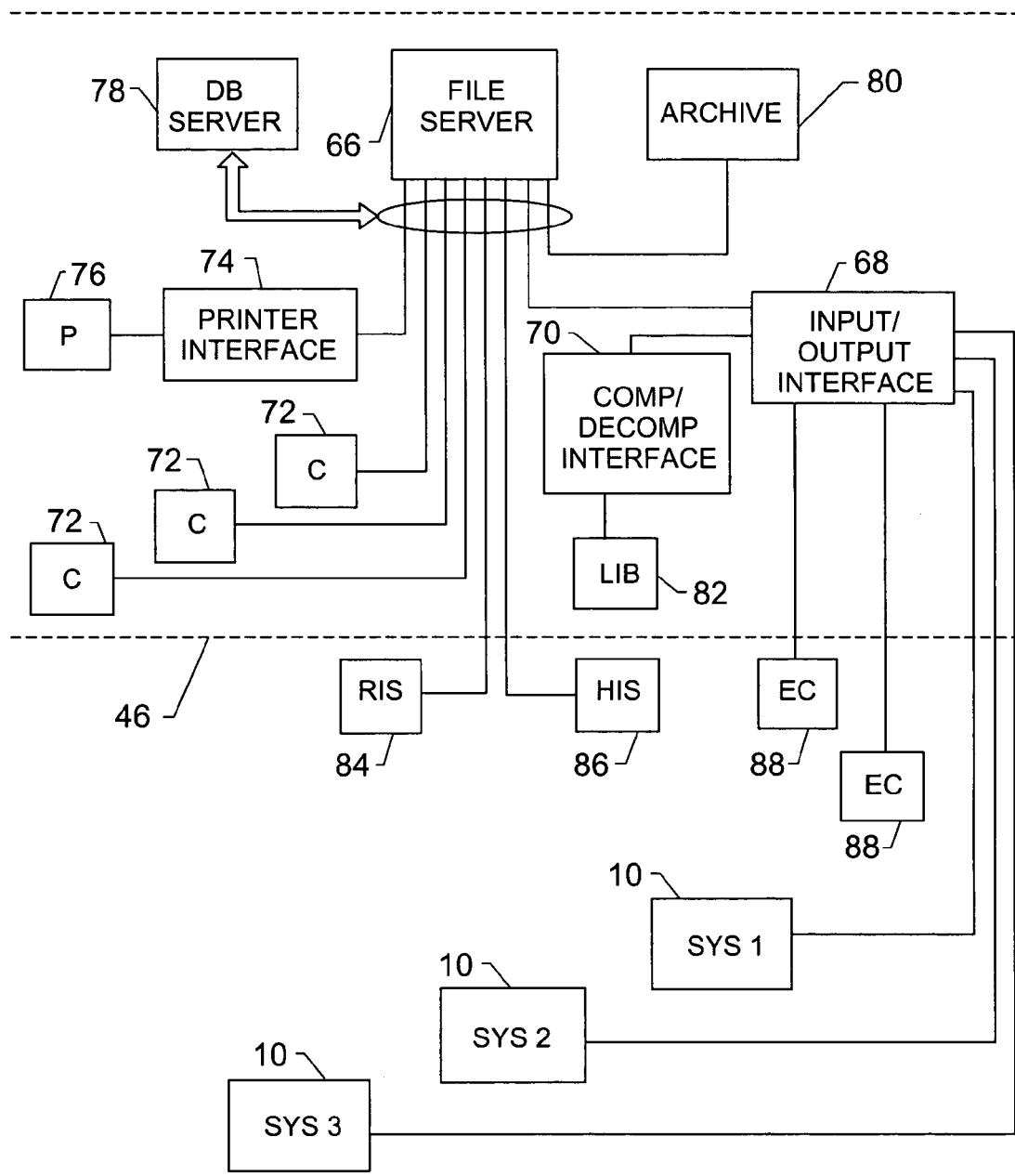
FIG. 3 is a diagrammatical representation of an exemplary image management system, in the illustrated example a picture archive and communications system or PACS, for receiving and storing image data in accordance with certain aspects of the present technique.

As noted above, the images generated by the system are typically stored in a PACS 46 (refer to FIG. 1). FIG. 3 illustrates an exemplary PACS 46 for receiving, storing and providing access to image data. In the illustrated embodiment, PACS 46 receives image data from several separate imaging systems, including system 10. PACS 46 includes one or more file servers 66 designed to receive and process image data, and to make the image data available for review. Server 66 receives the image data through an input/output interface 68. Image data may be compressed in routines accessed through a compression/decompression interface 70. In a typical system, interface 70 serves to compress the incoming image data rapidly and optimally, while maintaining descriptive image data available for reference by server 66 and other components of the PACS. Where desired, interface 70 may also serve to decompress image data accessed through the server. Compression of the data at the interface 70 may allow more data to be stored on the system 46 or may allow data to be transmitted more rapidly and efficiently to sites on the network which may also be configured to decompress the compressed data.

The server is also coupled to internal clients, as indicated at reference numeral 72, each client typically including a work station at which a radiologist, physician, or clinician may access image data from the server, decompress the image data, and view or output the image data as desired. Clients 72 may also input information, such as dictation of a radiologist following review of examination sequences. Similarly, server 66 may be coupled to one or more interfaces, such as a printer interface 74 designed to access and decompress image data, and to output hard copy images via a printer 76 or other peripheral.

A database server 78 may associate image data, and other work flow information within the PACS by reference to one or more file servers 66. In a presently contemplated embodiment, database server 78 may include cross-referenced information regarding specific image sequences, referring or diagnosing physician information, patient information, background information, work list cross-references, and so forth. The information within database server 78 serves to facilitate storage and association of the image data files with one another, and to allow requesting clients to rapidly and accurately access image data files stored within the system. Similarly, server 66 is coupled to one or more archives 80, such as an optical storage system, which serve as repositories of large volumes of image data for backup and archiving purposes. Techniques for transferring image data between server 66, and any memory associated with server 66 forming a short term storage system, and archive 80, may follow any suitable data management scheme, such as to archive image data following review and dictation by a radiologist, or after a sufficient time has lapsed since the receipt or review of the image files.

In the illustrated embodiment, other components of the PACS system or institution may be integrated with the foregoing components to further enhance the system functionality. For example, as illustrated in FIG. 3, a compression/decompression library 82 is coupled to interface 70 and serves to store compression routines, algorithms, look up tables, and so forth, for access by interface 70 (or other system components) upon execution of compression and decompression routines (i.e. to store various routines, software versions, code tables, and so forth). In practice, interface 70 may be part of library 82. Library 82 may also be coupled to other components of the system, such as client stations 72 or printer interface 74, which may also be configured to compress or decompress data, serving similarly as a library or store for the compression and decompression routines and algorithms. Although illustrated as a separate component in FIG. 3, it should be understood that library 82 may be included in any suitable server or memory device, including within server 66. Moreover, code defining the compression and decompression processes described below may be loaded directly into interface 70 and/or library 82, or may be loaded or updated via network links, including wide area networks, open networks, and so forth.

Additional systems may be linked to the PACS, such as directly to server 78, or through interfaces such as interface 68. In the embodiment illustrated in FIG. 3, a radiology department information system or RIS 84 is linked to server 66 to facilitate exchanges of data, typically cross-referencing data within database server 78, and a central or departmental information system or database. Similarly, a hospital information system or HIS 86 may be coupled to server 78 to similarly exchange database information, workflow information, and so forth. Where desired, such systems may be interfaced through data exchange software, or may be partially or fully integrated with the PACS system to provide access to data between the PACS database and radiology department or hospital databases, or to provide a single cross-referencing database. Similarly, external clients, as designated at reference numeral 88, may be interfaced with the PACS to enable images to be viewed at remote locations. Such external clients may employ decompression software, or may receive image files already decompressed by interface 70. Again, links to such external clients may be made through any suitable connection, such as wide area networks, virtual private networks, and so forth.

In addition to processing and refining the image data, the imaging system components may append certain information to the image data file. Such information may be included in an image data stream, such as in a header, or may be encoded directly in an image, such as by altering independent pixel values in one or more region of the image to provide contrast in the reconstructed image. Such contrasting pixels may be configured to comprise composite indicia that are readable by human viewers, such as text. In many instances, for example, patient identifying information may be "burned into" the images by permanently altering the image data itself, typically near boundary regions of the image to provide such information. As used herein, patient-identifying information should be understood to include patient name, patient numbers or reference characters, room numbers, social security numbers, or any other identifying information which can be linked to an individual patient. Other information and indicia may be provided in a similar manner. For example, a descriptive information indicating the type or location of anatomy viewable in the image, orientation of a particular image slice or frame, and so forth may be provided. Other such information may include dates on which the image was produced, hospitals, clinics or departments in which the image was produced, radiologists information, referring physician information, and so forth. Similarly, indicia maybe provided in the form of arrows, blocks, circles and other graphical tools to indicate features or anatomies of interest, and these may be associated with text, such as annotations, which draw a viewer's attention to such locations and provide an explanation of the basis for interest. The present technique provides an automated approach to identifying and obfuscating some or all such information, and particularly patient-identifying information.

Figure 4:
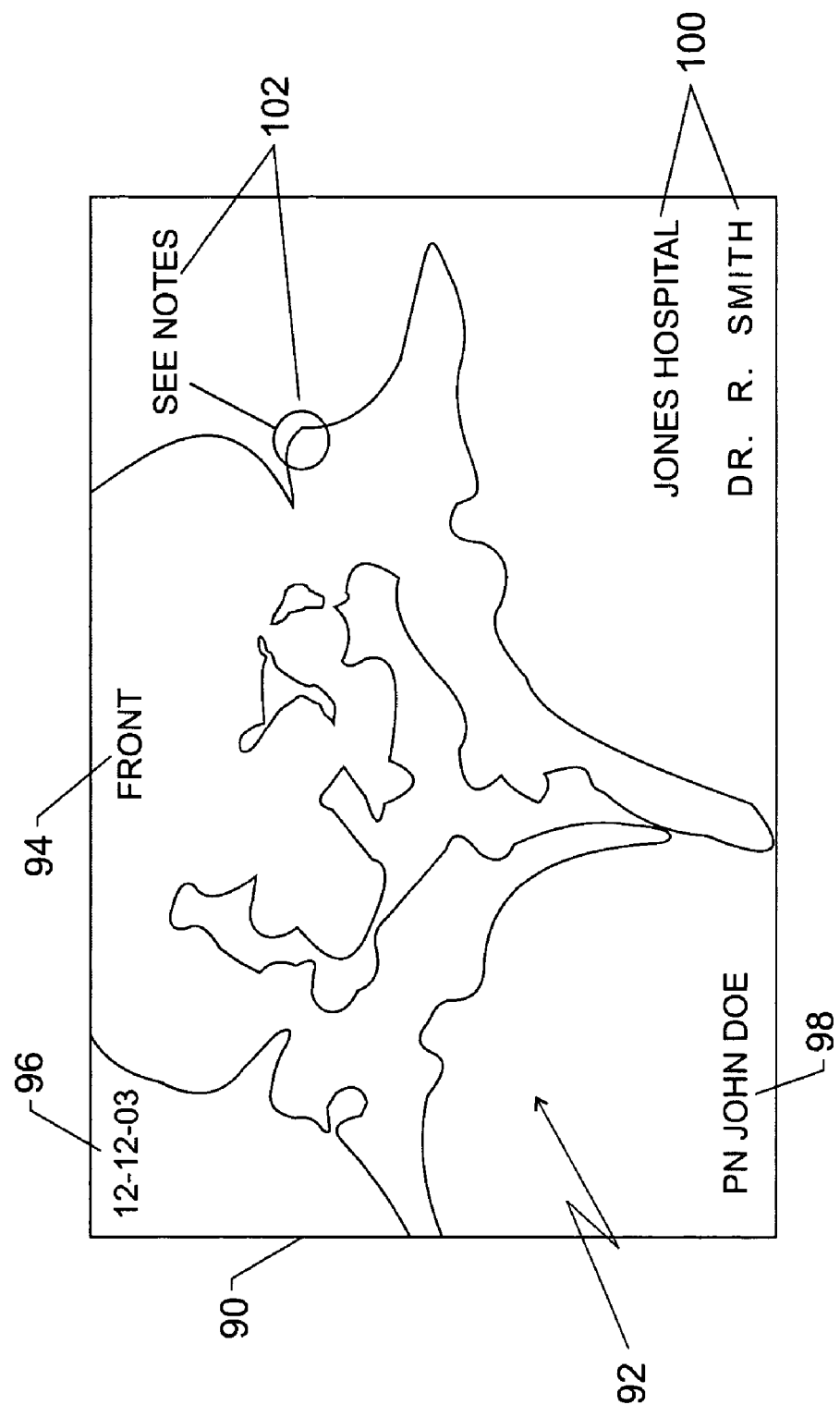
FIG. 4 is an exemplary medical diagnostic image produced by a system such as that described above and stored for viewing, and from which certain indicia should be masked or obfuscated in accordance with the present technique.

FIG. 4 represents an exemplary image of a pelvic region which may be acquired via a CT or other imaging system of the type described above, and stored and shared through the hospital systems described above. As illustrated in FIG. 4, the reconstructed image 90 presents subject matter 92 of interest, such as the internal anatomy of a patient. Descriptive information 94 provides an indication of an orientation or, more generally, the nature of the image. Date information is provided as indicated by reference numeral 96. Patient-identifying information 98 is provided to permit appropriate diagnosis based upon the image. Similarly, hospital and physician information is provided as indicated at reference numeral 100. Finally, certain indicators and annotations are provided as represented at reference numeral 102 for drawing a viewer's attention to specific areas of interest and for explaining the reasons for interest in the areas. As will be appreciated by those skilled in the art, such information is typically "burned into" the digitized image by permanently altering the data descriptive of individual pixels. That is, the digital value of certain pixels in the image are altered to provide contrast with adjacent pixels, and thereby to define the letters and other indicia that form the human-readable words. High contrast values are typically employed, such as values near an upper or lower limit of the dynamic range of the pixels.

Figure 5:
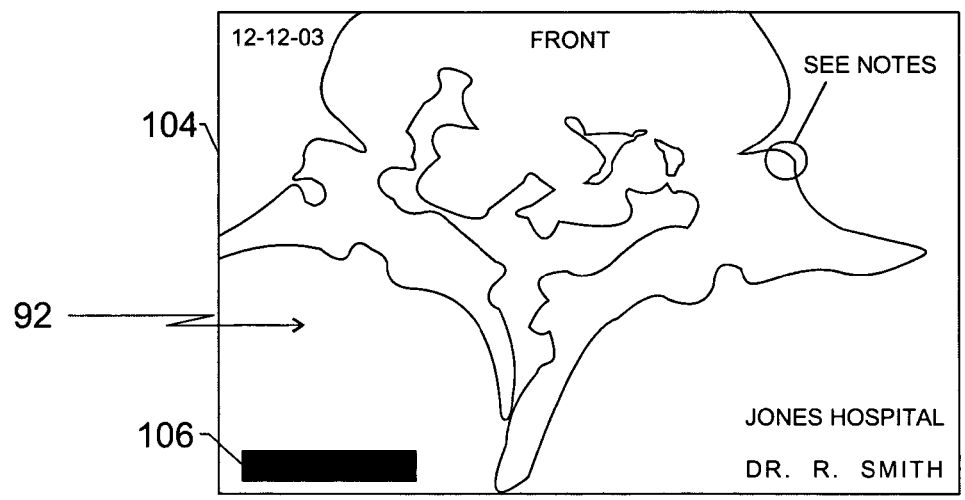
FIG. 5 is a view of the image of FIG. 4 in which patient-identifying indicia have been masked.
Figure 6:
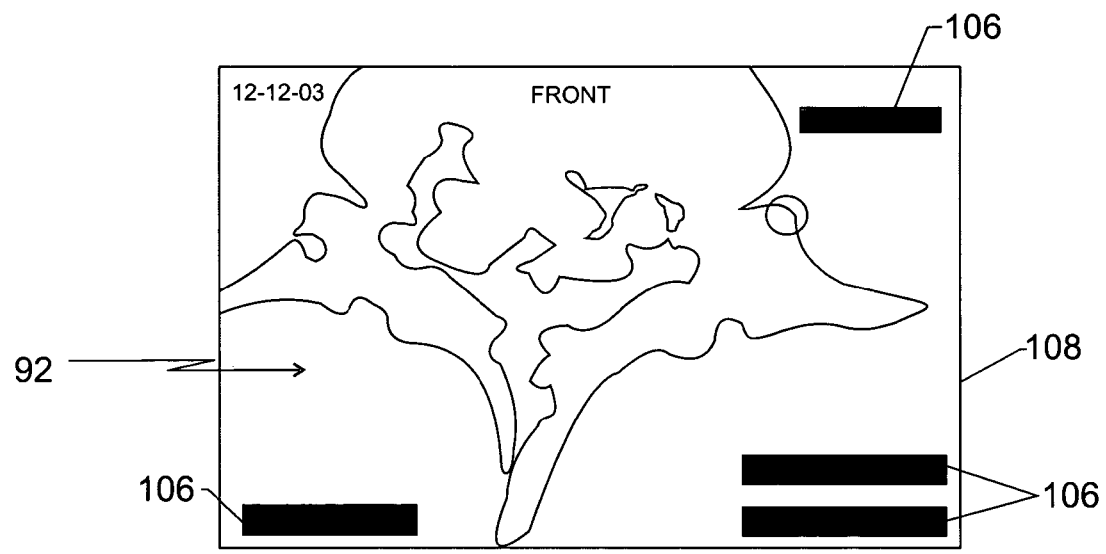
FIG. 6 is a similar image in which additional information relating to physician and hospital identification and annotations have been masked.
Figure 7:
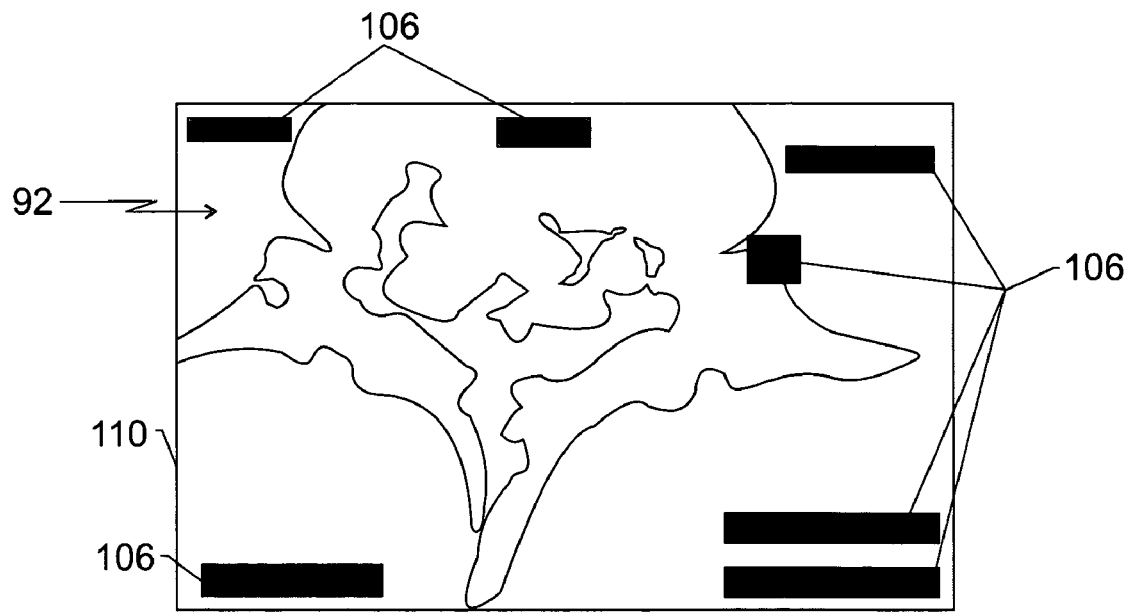
FIG. 7 is a similar image view in which all human readable indicia have been masked.

It should be noted that the present technique is generally applied to the reconstructed image, as opposed to data included in other image domains. As will be appreciated by those skilled in the art, depending upon the imaging modality, processing proceeds through multiple domain, such as k-space in magnetic resonance imaging, Radon in CT imaging, and so forth. Similarly, existing techniques provide for removal of data in conventional image headers. However, conventional techniques do not typically address the presence of "burned in" indicia in reconstructed images. Accordingly, the present technique allows for removal of obfuscation of certain indicia in the final reconstructed image. In particular, it is presently preferred that patient-identifying information be masked in the reconstructed image by replacing the data in a region of the image with masking data values. That is, where pixels have been altered to define human-readable indicia, the indicia are rendered undecipherable in the reconstructed image by identifying limits of the region and then altering pixels in a region to avoid all available contrast which would render indicia discernible or decipherable. FIGS. 5, 6 and 7 illustrate examples of such maskings.

As shown in FIG. 5, the image of FIG. 4 has been processed to mask a region in which the patient-identifying information 98 was visible (see FIG. 4) by replacing the entire region with replacement data 106. The replacement data effectively covers the entire region and alters all pixel values in a region to render the indicia or text undecipherable. In general, the pixel values may be altered by changing both the values of the indicia pixels and the surrounding pixels to the same pixel intensity. Other approaches may, of course, be adopted, such as providing for randomized values, blended values, and so forth. In the resulting processed image 104, then, the patient-identifying information is not visible, and the replacement data 106 covers the region where the indicia were formally viewable.

FIG. 6 represents a further processed image 108 in which multiple regions of information 106 have been masked. In the image of FIG. 6, however, the masked information includes regions where a patient-identifying information was presented, as well as information relating to the physician and hospital, and annotations which may have been added by the physician. As with the image of FIG. 5, the date and descriptive information have been left in the image.

FIG. 7 represents a further processed image 110 in which all indicia in the image have been rendered undecipherable. The subject matter 92 of the image is still clearly visible, but the indicia have been masked or obfuscated completely from the view.

Figure 8:
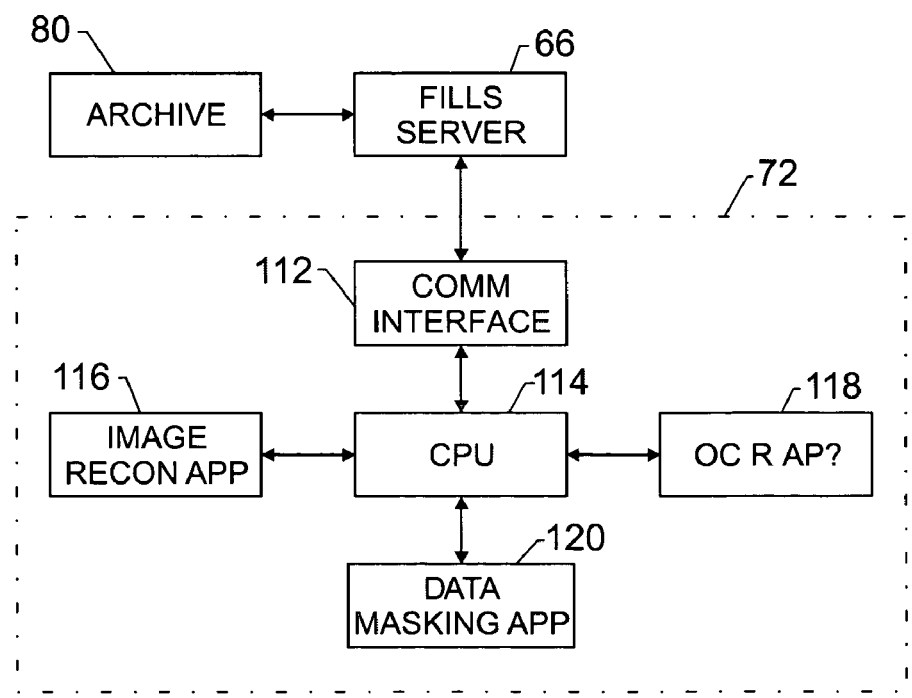
FIG. 8 is a diagrammatical representation of a system for recognition of indicia to be rendered undecipherable in a reconstructed image in accordance with the present technique.

As noted above, the present technique is preferably implemented on an automated basis requiring little or no operator intervention. FIG. 8 is a diagrammatical representation of certain functional components of the system as it might be implemented in practice. As noted in the foregoing presentation, a file server 66 is available to provide images that are stored in an image archive 80. Various configurations can be used for archiving and serving of the file, both networked and stand-alone. At a client workstation 72, specific modules or functional components are provided for recognizing and masking the indicia to be rendered undecipherable in the reconstructed images.

As shown in FIG. 8, the workstation on which the masking operations are performed includes a series of hardware and software components that permit recognition of the indicia to be masked, and alteration of the image data to provide the desired masking in the regions where the indicia appear. The work station preferably includes a communications interface 112 which is designed to request and receive image data from the file server 66. The communications interface is coupled to a center processing unit 114 which performs the image analysis and alteration operations. The CPU 114 may be part of a general purpose or application-specific computer system, and the system may include a wide variety of additional components, depending upon the other functions it is called upon to perform. In some applications, the workstation itself may be a PACS workstation of the type described above. An image reconstruction application 116 is provided that allows for reconstruction of the image as it will be viewed by a user. As will be apparent to those skilled in the art, the image reconstruction application will vary depending upon the image type, the image encoding scheme, the imaging modality, and similar factors. An optical character recognition application 118, or any other suitable indicia recognizing application is provided which is called upon by the CPU to recognize indicia encoded in the reconstructed images that can be deciphered or read by a human viewer. In particular, the optical character recognition application 118 permits recognition of text, both vertically and horizontally oriented, and where appropriate in multiple languages. A data masking application 120 is further provided which includes code appropriate for altering pixel values in locations corresponding to a region in which indicia appear that are to be rendered undecipherable in the final reconstructed image. It should be noted that other appropriate programming and applications may also be provided in the workstation. For example, as noted below, comparison routines may be implemented, for example in the data masking application or the optical character recognition application, that permit certain types of information or terms to be distinguished from other terms which can be masked. For example, dates and descriptive information, such as image orientation, image type, and the like, may be listed or otherwise identified to avoid masking such information in the masking operation. Such distinctions may be made by simple comparisons of text, text formats, look-up tables of terms to be masked or left unmasked, and so forth.

Figure 9:
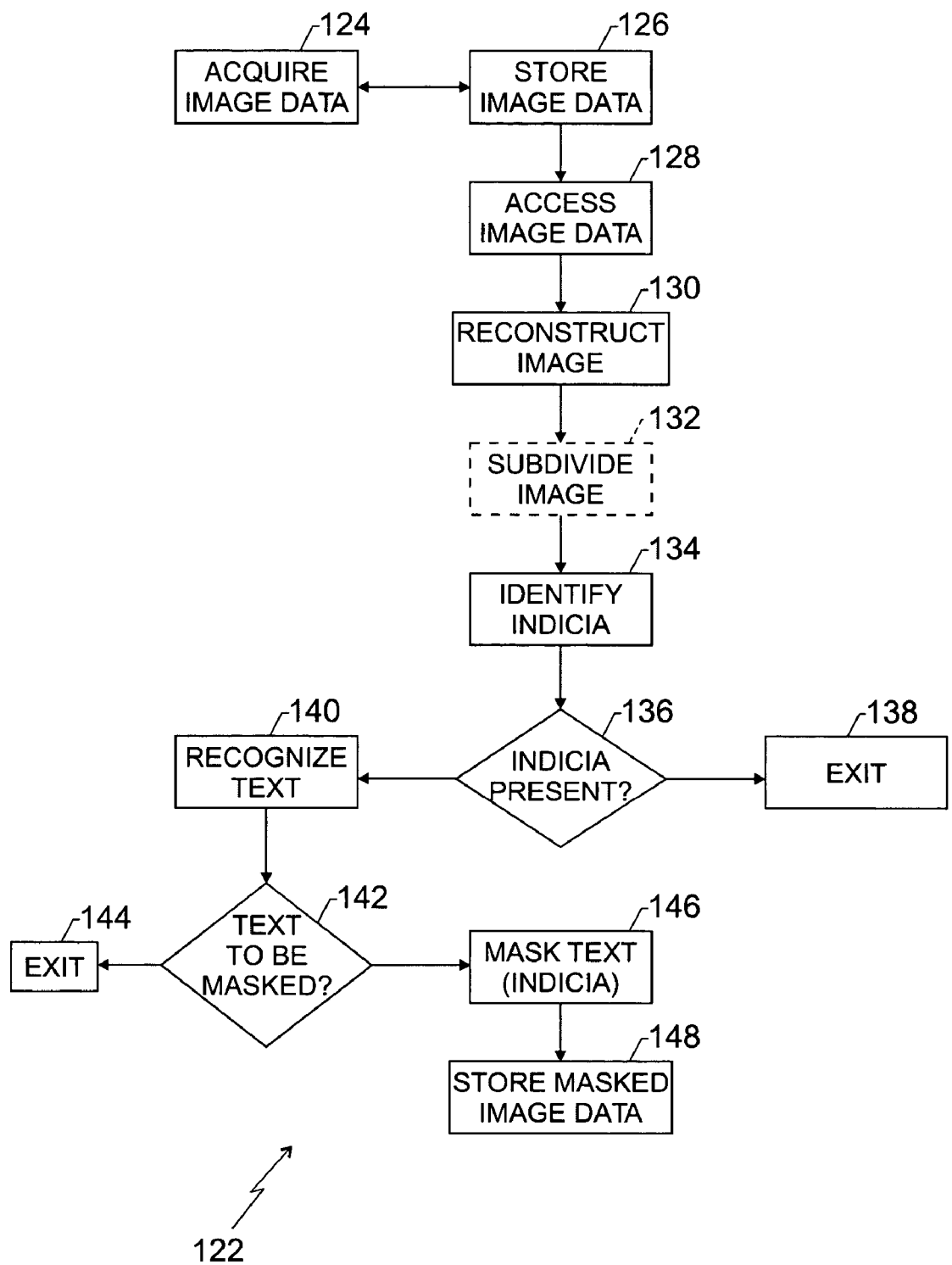
FIG. 9 is a flow chart illustrating exemplary logic in a process for recognizing and masking indicia through the system of FIG. 8.

Exemplary logic, designated by reference numeral 122, implemented by the system of FIG. 8 is illustrated generally in FIG. 9. As noted above, the process leading to the present technique begins with acquisition of image data at step 124, and storage of the image data at step 126. Software and routines for caring out the present technique may, however, be completely independent of the acquisition and storing functions. Indeed, the present techniques may be carried out on completely separate workstations at or remote from a facility in which the image data is acquired or created, processed and stored.

At step 128 the image data is accessed from an appropriate storage medium. At step 130 the image reconstruction application, discussed above, is called upon to reconstruct the image. As noted, the present technique is preferably applied to reconstructed images so as to ensure obfuscation of indicia which could be discernible in the reconstructed image. Other techniques may supplement the present technique to delete or otherwise render indiscernible specific data embedded in a data stream, such as in the header section of image data. At step 132 the image may be subdivided into strips or regions. This optional step can serve to facilitate the analysis of the overall image. When the image is subdivided, the subsequent steps of identifying indicia and treating the indicia are preferably carried out on the basis of the individual subdivisions.

At step 134 indicia are identified in the image by analysis of the pixels representing the indicia, commonly text, such as by the optical character recognition application discussed above. At step 136 the routine determines whether such indicia have been identified. If no such indicia have been identified, the routine may exit at step 138, and the image data is essentially unaltered. If such indicia are identified in the image or in the subdivision of the image, an attempt is made to recognize the text at step 140. Again, step 140 will typically be carried out by an optical character recognition application, which may be set to recognize text alone or specific symbols or annotations. If such text or indicia are recognized, the routine determines whether the indicia are to be masked, as indicated at step 142. As noted above, step 142 may include a comparison of specific indicia to a list of indicia, formats for indicia, or any other suitable basis for distinguishing text or indicia that should be rendered indiscernible in the final image from indicia that should be left viewable and readable. Again, by way of example, such indicia that may be left in the image may include descriptive information, dates, and so forth, as represented in FIGS. 5 and 6 above. If no text is to be masked at step 142, the routine may exit at step 144. On the contrary, if text or indicia are to be masked, the masking operation is performed at step 146.

As noted above, the masking operation of step 146 may be carried out through a specific application in the processing workstation. The masking operation essentially identifies a region bounding the indicia to be masked, and alters the pixel values for the region so as to render the indicia undecipherable. In a presently contemplated embodiment, for example, the pixels are given the same intensity value so as to render any text that would have been in the region undecipherable due to the complete lack of contrast with neighboring pixels in the region. Finally, at step 148 the masked image data is stored for later retrieval. The masked image may be stored over or separately from the original image data which, for diagnostic purposes, may be maintained as an archival copy. The mask data set is, however, useful where it is to be shared or transmitted to other entities or persons with no right or need to see the masked information.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A computer-implemented method for processing digital images comprising:
on a physical computing processor:
analyzing image data to identify indicia apparent in an image reconstructed from the image data;
identifying one or more region in which the indicia appear in the image, including text in horizontal and vertical orientations;
comparing the indicia to a list of indicia to remain decipherable or to a list of indicia to be rendered undecipherable in the reconstructed image; and
based upon the comparison, replacing image data for at least one region with replacement data to render indicia undecipherable in an image reconstructed from the image data.

2. The method of claim 1, wherein the identifying indicia include text defined by pixels of the image reconstructed from the image data.

3. The method of claim 1, wherein the indicia are identified by optical character recognition.

4. The method of claim 1, wherein the replacement data masks the one or more region with a substantially uniform pixel intensity.

5. The method of claim 1, comprising identifying indicia to remain decipherable in the image reconstructed from the image data, and wherein the step of replacing the image data only replaces data for the at least one region and not for regions in which the indicia to remain decipherable appear.

6. The method of claim 1, comprising allowing desired indicia to remain decipherable in the image reconstructed from the image data.

7. The method of claim 6, wherein the desired indicia include indicia providing a general description of the image subject matter or a date.

8. The method of claim 1, wherein the image data represents a medical diagnostic image, and wherein indicia rendered undecipherable include patient identifying indicia.

9. The method of claim 1, wherein the image data encodes a grey scale image.

10. A computer-implemented method for processing digital images comprising:
on a physical computing processor:
analyzing image data via optical character recognition to identify textual indicia apparent in an image reconstructed from the image data;
identifying one or more region in which the indicia appear in the image, including text in horizontal and vertical orientations;
comparing the identified textual indicia to a list of textual indicia to remain decipherable in the reconstructed image; and
based upon the comparison, replacing image data for at least one region with replacement data to render indicia in the at least one region undecipherable in an image reconstructed from the image data, and wherein textual indicia to remain decipherable in the reconstructed image is not replaced with replacement data.

11. The method of claim 10, wherein the image data represents a medical diagnostic image, and wherein the undesired indicia include patient identifying indicia.

12. The method of claim 10, wherein the textual indicia to remain decipherable include indicia providing a general description of the image subject matter or a date.

13. The method of claim 10, wherein the replacement data masks the one or more region with a substantially uniform pixel intensity.

14. A computer-implemented method for processing digital images comprising:
on a physical computing processor:
analyzing medical diagnostic image data via optical character recognition to identify textual indicia including indicia of patient identity apparent in an image reconstructed from the image data;
identifying one or more region in which the indicia appear in the image, including text in horizontal and vertical orientations;
comparing the identified textual indicia to a list of textual indicia to be rendered undecipherable in the reconstructed image; and
based upon the comparison, replacing image data for one or more regions in which textual indicia is to be rendered undecipherable with replacement data to render the indicia undecipherable in an image reconstructed from the image data.

15. The method of claim 14, wherein the textual indicia to remain decipherable include indicia providing a general description of the image subject matter or a date.

16. The method of claim 14, wherein the replacement data masks the one or more region with a substantially uniform pixel intensity.

17. A system for processing digital images comprising:
means for analyzing image data to identify indicia apparent in an image reconstructed from the image data;
means for identifying one or more region in which the indicia appear in the image, including text in horizontal and vertical orientations;
means for comparing the indicia to a list of indicia to remain decipherable or to a list of indicia to be rendered undecipherable in the reconstructed image; and
means for replacing image data for at least one region with replacement data to render indicia undecipherable in an image reconstructed from the image data based upon the comparison.

18. A system for processing digital images comprising:
means for analyzing image data via optical character recognition to identify textual indicia apparent in an image reconstructed from the image data;
means for identifying one or more region in which the indicia appear in the image, including text in horizontal and vertical orientations;
means for comparing the identified textual indicia to a list of textual indicia to remain decipherable in the reconstructed image; and
means for replacing image data for at least one region with replacement data to render indicia in the at least one region undecipherable in an image reconstructed from the image data, and wherein textual indicia to remain decipherable in the reconstructed image is not replaced with replacement data based on upon the comparison.

19. A system for processing digital images comprising:
means for analyzing medical diagnostic image data via optical character recognition to identify textual indicia including indicia of patient identity apparent in an image reconstructed from the image data;
means for identifying one or more region in which the indicia appear in the image, including text in horizontal and vertical orientations;
means for comparing the identified textual indicia to a list of textual indicia to be rendered undecipherable in the reconstructed image; and
means for replacing image data for one or more regions in which textual indicia is to be rendered undecipherable with replacement data to render the indicia undecipherable in an image reconstructed from the image data based upon the comparison.

20. A computer program for processing image data comprising:
at least one computer readable medium; and
code stored on the at least one computer readable medium encoding routines for analyzing image data to identify indicia apparent in an image reconstructed from the image data, identifying one or more region in which the indicia appear in the image, including text in horizontal and vertical orientations, comparing the indicia to a list of indicia to remain decipherable or to a list of indicia to be rendered undecipherable in the reconstructed image, and replacing image data for at least one region with replacement data to render indicia undecipherable in an image reconstructed from the image data based upon the comparison.

21. A computer program for processing image data comprising:
at least one computer readable medium; and
code stored on the at least one computer readable medium encoding routines for analyzing image data via optical character recognition to identify textual indicia apparent in an image reconstructed from the image data, identifying one or more region in which the indicia appear in the image, including text in horizontal and vertical orientations, comparing the identified textual indicia to a list of textual indicia to remain decipherable in the reconstructed image, and replacing image data for at least one region with replacement data to render indicia in the at least one region undecipherable in an image reconstructed from the image data, and wherein textual indicia to remain decipherable in the reconstructed image is not replaced with replacement data based upon the comparison.

22. A computer program for processing image data comprising:

at least one computer readable medium; and code stored on the at least one computer readable medium encoding routines for analyzing medical diagnostic image data via optical character recognition to identify textual indicia including indicia of patient identity apparent in an image reconstructed from the image data, identifying one or more region in which the indicia appear in the image, including text in horizontal and vertical orientations, comparing the identified textual indicia to a list of textual indicia to be rendered undecipherable in the reconstructed image, and replacing image data for one or more regions in which textual indicia is to be rendered undecipherable with replacement data to render the indicia undecipherable in an image reconstructed from the image data based upon the comparison.

* * * * *

UNITED STATES PATENT AND TRADEMARK OFFICE
CERTIFICATE OF CORRECTION

PATENT NO. : 7,627,152 B2 Page 1 of 1
APPLICATION NO. : 10/723033
DATED : December 1, 2009
INVENTOR(S) : Mathew et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1303 days.

Signed and Sealed this

Second Day of November, 2010

David J. Kappos
*Director of the United States Patent and Trademark Office*